United States Patent
Ibsen et al.

(10) Patent No.: US 6,224,372 B1
(45) Date of Patent: May 1, 2001

(54) THIN FILM DENTURE RELINER BONDING AID AND A PROCESS OF SECURING DENTURES IN THE ORAL CAVITY

(75) Inventors: Robert L. Ibsen; Elizabeth A. Karleskint, both of Santa Maria, CA (US)

(73) Assignee: Den-Mat Corporation, Santa Maria, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/872,969

(22) Filed: Jun. 11, 1997

(51) Int. Cl.[7] ................................................. A61C 13/02
(52) U.S. Cl. ................................................... 433/168.1
(58) Field of Search .................... 433/37, 48, 214, 433/213, 168.1

(56) References Cited

U.S. PATENT DOCUMENTS

| | | | |
|---|---|---|---|
| 4,470,814 | * | 9/1984 | Chang et al. ................ 433/168.1 X |
| 4,608,088 | * | 8/1986 | Lokken .................................. 406/35 |
| 4,632,880 | * | 12/1986 | Lapidus ......................... 433/168.1 X |
| 4,664,630 | * | 5/1987 | Lokken ................................ 433/180 |
| 4,979,989 | * | 12/1990 | Ridoux ............................ 433/214 X |
| 5,076,790 | * | 12/1991 | Rollison et al. ..................... 433/214 |
| 5,158,825 | * | 10/1992 | Altwirth ............................... 428/286 |
| 5,698,610 | * | 12/1997 | Futami et al. .................. 433/214 X |

* cited by examiner

*Primary Examiner*—Nicholas D. Lucchesi
(74) *Attorney, Agent, or Firm*—Dorsey & Whitney LLP

(57) ABSTRACT

A process for bonding a denture to the tissue surfaces of the jaw over which the denture is superimposed during use which comprises the steps of providing at the interface of the denture and the jaw's tissues, a liquid irreversible hydrocolloid of an alginate dental impression formulation, applying pressure to the denture so that it presses into the tissue surfaces and causes the liquid hydrocolloid to flow within such interface, and then allowing the hydrocolloid to solidify within the interface. Also described is a novel relatively-thin film, settable hydrocolloid denture aid and the set, cushiony, relatively-thin film denture aid obtained from it.

37 Claims, 1 Drawing Sheet

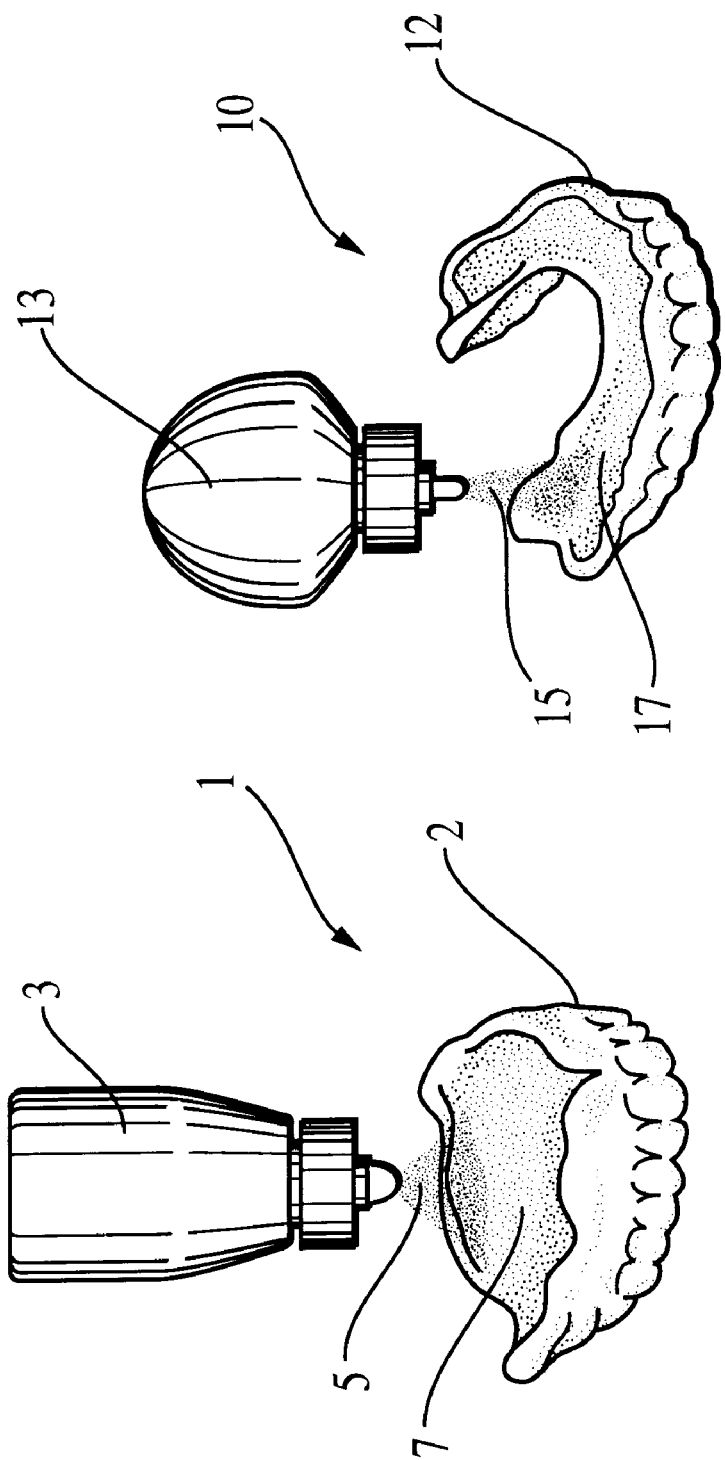

THIN FILM DENTURE RELINER BONDING AID AND A PROCESS OF SECURING DENTURES IN THE ORAL CAVITY

BRIEF DESCRIPTION OF THE INVENTION

The invention relates to a relatively thin film denture bonding aid and reliner, its precursor film and a method for securing a denture to a user's gum and/or oral mucosa (inclusive of the palate). The thin film denture aid of the invention comprises alginate hydrocolloid forming powder. It is placed on the denture surface that contacts the gum, and through contact with saliva or water is converted into a hydrocolloid that functions as a reliner for the denture.

BACKGROUND TO THE INVENTION

A denture (or dental plate) is a partial or complete set of removable artificial teeth for either the upper or lower jaw that is typically constructed of acrylic resin alone or in conjunction with various metals. A complete denture is a full denture which replaces the whole of the normal dentition in the dental arch with the exception of the third molars. The denture base is that part of the denture which rests on the oral mucosa (mucous membrane). As noted above, dentures are generally made from acrylic resins, and typically made by the dough molding and curing technique.

A properly fitted denture, that is, a denture whose base surface perfectly replicates the gums or the oral mucosa with which it contacts, will adhere to the gum or oral mucosa for an extended period of time, typically for a whole waking day for the patient. However, dentures seldom properly fit the gum or oral mucosa, and as a result, the patient requires a bonding aid, typically a weak a weak adhesive, or a difficult-to-use sheet material that functions as a reliner. A common characteristic of most of these weak adhesives is that they leave a hard-to-remove residue on either the jaw or oral mucosa, and/or the denture's base surface, after the denture is removed from the patient's mouth. This necessitates extensively rinsing the mouth to clean the oral surfaces affected and/or extensively rinsing the denture to clean the base surfaces affected.

Denture bonding aids come in a variety of forms. For example, Super PoliGrip® (Block Drug Company, Inc.) is an adhesive that is sold in the form of a small particle powder and a cream. RoVal Super Strength denture adhesive cream (distributed by Rock Bottom Stores) is a thick paste-like cream that appears to get lumpy when mixed with water. Fixodent® (distributed by Proctor & Gamble) is a denture adhesive that comes as a finely ground powder that is easily suspended in air when forced from its squeezable dispenser. SuperWernet's® (sold by Block Drug Company, Inc.) is stated to be a denture adhesive powder. When dispensed from its container, it too creates a dusty powdery mass, on or about the denture. Dentrol® (sold by Block Drug Company, Inc.) is a liquid denture adhesive that appears to leave a residue on the denture that requires removing. Ezo® denture cushions (sold by Medtech Laboratories, Inc.) are thick wax-like pads that are wetted in order to shape them to the base surface of the denture. Clearly, they act as relining surfaces that utilize their surfaces as the bonding surface to the gum and to the denture's base surfaces. The thickness of the pads suggest that they alone determine adherence of the denture to the jaw and the adhesion is dependent on the joint bonding of the pads to the jaw and the denture. Polident® Dentu-Grip® (sold by Block Drug Company, Inc.) is another denture adhesive powder, that appears to have the characteristics of the aforementioned adhesive powders. Poli-Grip® Free (sold by Dento, Inc.) is another denture adhesive paste (characterized as a cream). Poli-Grip® (sold by Block Drug Company, Inc.) is another denture adhesive paste. It appears to be the same as Poli-Grip® Free except for color and name. A similar adhesive paste is sold under the name of Butler® Secure® (John O. Butler Co.). Rigident® (sold by Carter Products, Div. of Carter-Wallace, Inc.) is another denture adhesive powder that has the characteristics of the other adhesive powders described above. Sea-Bond® denture adhesive (Combe Incorporated) is an adhesive laden non-woven textile pad that swells and softens when wetted with water.

A denture is intended to perfectly fit on the oral tissues to which it is fitted. However, dentures are not always perfectly made, or because of soft tissue changes in the user's mouth that occur during the wearing of a denture, it is often necessary to change the denture's tissue surface (i.e., the denture's base) to conform it to the new tissue contours and occlusal relationships. Demonstrative of this are the procedures that dentists employ to readapt the denture by either rebasing or relining the denture. In denture relining, new resin of some type is added to the existing denture base. In rebasing a denture, an impression is taken of the soft tissues by using the existing denture as an impression tray. A stone cast is then constructed in the corrected denture. The denture and cast are mounted in a specially designed device which will maintain the correct vertical and horizontal relationship between the cast and the denture teeth. After the teeth are indexed for position, the denture is removed and the teeth are separated from the old denture base. The teeth are then reassembled in the index of the mounting device and held in their original relationship to the cast while they are waxed to the new base plate. From this point conventional procedures are followed and a new denture base processed. In other words, A new denture is constructed using the same teeth as before. The denture relining procedure involves an impression of the soft tissues using the existing denture as an impression tray. A stone cast is constructed in the corrected denture after which the cast with the attached denture is invested in a flask. When the flask halves are separated, the impression material is removed from the denture, and new acrylic resin is cured against the old by the usual compression molding technique. From the standpoint of denture stability, the rebasing process is preferred to the relining technique.

Tissue conditioners or temporary soft reliners are materials that are used only for a short period of time, typically for a few days. Oral tissues may become inflamed and distorted under certain conditions of health debilitation or ill fitting dentures. Relining the ill fitting denture with a tissue conditioner allows the tissue to return to "normal," during which time a new denture can be made. These tissue conditioners are primarily highly plasticized acrylic resins. They are supplied as a powder and a liquid. The composition of the powdered polymer is generally a poly(ethyl methacrylate) or one of its copolymers, while the liquid is an aromatic ester (butyl phthalate butyl glycolate) in ethanol or an alcohol of high molecular weight. These are mixed together to form a gel. As with other relining procedures, the denture base is relieved on the tissue surface and the dough or gel inserted. When the denture placed in the mouth, the gel flows readily to fill the space between the denture base and the oral tissue. The tissue conditioners, like the "permanent" resilient liners, can absorb energy elastically; however, unlike permanent resilient materials, the tissue conditioners also undergo viscous flow under load. Thus, they change their form with the changing contour of the supporting tissue so that good adaptation of the denture to the tissue is maintained. It also has been stated that the conditioner can massage the underlying tissue and stimulate blood circulation. As tissue conditioners age they lose their plastic properties, and the elastic characteristic becomes dominant. When this occurs, if the problem has not been corrected, it may be necessary to replace the old tissue conditioner with new material. Some individuals may use the denture with the tissue conditioner as an impression from which a gypsum model is obtained for construction of the new denture.

Since the most important characteristics of the tissue conditioners are their rheological properties, their behavior in the oral cavity is stated to be as follows: The initial mix is a free-flowing liquid which requires 16 or 20 minutes to develop plastic properties (form a strain rate sensitive gel). The formation of elastic characteristics varies with different products, ranging from several hours to several days. In the end, the elastic properties are lost when the alcohol and plasticizer are leached from the resin.

In the case of all of the aforedescribed denture bonding aids, each in its fashion attempts to function as a reliner for the denture. How effective they are in that task depends on whether they simply fill the voids between the denture base and the jaw and whether they also fill where the denture and the jaw have excellent fit and relining is not needed or desired. If they interfere with a good fit between the denture and the jaw, then the material will be an ineffectual bonding aid. For example, the pads cover the whole of the denture base, and thus interfere with the fit of the denture to the jaw where the fit would otherwise be excellent. In the case of the paste adhesives, they are messy to use and require expert metering to the denture's base in order to avoid an excessive or a deficient amount being applied to the base. If the amount applied is excessive, then the user is required to wipe away or swallow paste that exudes from between the denture base and the jaw portion to which it is applied. If the amount is deficient, then the denture will be ineffectively bonded to the jaw. In addition, the high viscosity of such pastes makes it difficult to avoid coating the interface between the denture base and the jaw where the fit of the denture is excellent. Consequently, the paste interferes with the fit of the denture to the jaw. The powder adhesives are difficult to uniformly apply to the denture base, and as a result, the ability of the powder adhesives to function as a reliner is dependent on their ability, once wet, to properly flow-realign on the denture base to the pressure imposed when the denture is fitted on the jaw. In all instances noted, the paste adhesives when wetted by water have too high a viscosity to properly flow-realign at the denture base-jaw interface.

Alginates are salts of alginic acid (obtained from seaweed) which, when mixed with water in the recommended proportions, forms an irreversible hydrocolloid gel used for dental impressions. This chief ingredient of the irreversible, hydrocolloid impression materials is one of the soluble alginates. It is generally conceded to be a linear polymer of the sodium salt of anhydro-beta-d-mannuronic acid with the following structural formula:

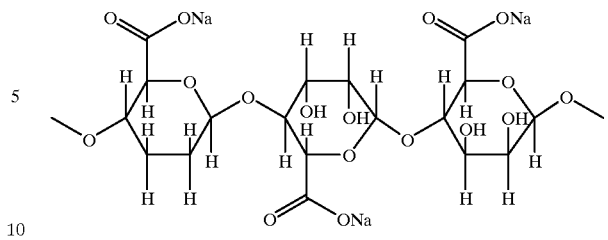

Alginic acid is insoluble in water, but some of its salts are not. The acid can be changed to a salt very readily, since the polar carboxyl groups are free to react. Most of the inorganic salts are insoluble, but its sodium, potassium, and ammonium salts are soluble in water. Sodium, potassium, and triethanol amine alginate are used in dental impression materials. When mixed with water the water-soluble alginates form a sol similar to the agar sol. The sols are quite viscous even in low concentrations, but the water soluble alginates, useful in dentistry, form sols quite readily if the alginate powder and water are mixed vigorously. The molecular weight of the alginate compounds may vary widely, depending on the manufacturing treatment. The greater the molecular weight, the more viscous is the sol.

Manufacturers supply the dentist with the alginate powder, containing the added ingredients discussed below. The dentist prepares the alginate sol of the proper viscosity and places it in the mouth in an impression tray. Gelation occurs by chemical reaction and the impression is then removed. The procedure differs essentially from that employed with the reversible hydrocolloid materials in that the dentist prepares the sol himself and the temperature is not an active factor in gelation.

There are a number of methods for the production of this chemical, but the simplest and best understood method is to react the sol alginate with calcium sulfate to produce insoluble calcium alginate as a gel. Practically, such a reaction must take place in the mouth; therefore, it must be delayed while the impression material is mixed with water, placed in the impression tray, and carried to the mouth. The reactions are best illustrated by a typical example.

Calcium sulfate is an excellent compound for the production of an insoluble calcium alginate when it reacts with potassium or sodium alginate in an aqueous solution. In practice, the production of the calcium alginate is delayed by the addition of a third soluble salt to the solution, with which the calcium sulfate will react in preference to the soluble alginate to form an insoluble calcium salt. Thus, the reaction between the calcium sulfate and the soluble alginate is prevented so long as any of the added salt is left.

The added salt is known as a "retarder." There are a number of soluble salts which can be used as the retarder. They include alkali metal salts of weaker acids than the acid used in the "reactor," such as sodium or potassium phosphate, oxalate, or carbonate. Trisodium phosphate, sodium tripolyphosphate, and tetrasodium pyrophosphate have been employed, but the latter two are now the most commonly used. The calcium sulfate, or whatever chemical is used to produce the gel, is known as the "reactor."

For example, if suitable amounts of calcium sulfate, potassium alginate, and trisodium phosphate are mixed together in proper proportions in water, after they become partially or totally dissolved the following reaction will take place:

$$2Na_3PO_4 + 3CaSO_4 \rightarrow Ca_3(PO_4)_2 + 3Na_2SO_4 \quad (I)$$

When the supply of trisodium phosphate is exhausted, the calcium ions begin to react with the potassium alginate to produce a cross-linked calcium alginate as follows:

$$K_nAlg + \tfrac{1}{2}CaSO_4 \rightarrow \tfrac{1}{2}K_2SO_4 + Ca+e, fra \; n/2 + ee \; Alg \quad (II)$$

A formulation for an alginate impression material based upon the reactions shown above, is as follows (in per cent, by weight):

| | |
|---|---|
| Potassium alginate | 15% |
| Calcium sulfate | 16% |
| Zinc oxide | 4% |
| Potassium titanium fluoride | 3% |
| Diatomaceous earth | 60% |
| Sodium phosphate | 2% |

The exact proportion of each chemical to be used varies with the type of raw material. Particularly, the amount of retarder (sodium phosphate) must be adjusted carefully to provide the proper gelation time. In general, if approximately 15 grams of the powder is mixed with 40 ml of water, gelation will occur in about 3 to 4 minutes at normal room temperature.

The purpose of the diatomaceous earth is to act as a filler. The filler, if added in proper amounts, can increase the strength and stiffness of the alginate gel, produce a smooth texture, and insure a firm gel surface that is not tacky. It also aids in forming the sol by dispersing the alginate powder particles in the water. Without a filler, the gel formed lacks firmness and exhibits a sticky surface covered with a syneretical exudate. The zinc oxide also acts as a filler and has some influence on the physical properties and setting time of the gel.

Any type of calcium sulfate can be used as the reactor. The dehydrate form is generally used, but under certain circumstances the hemihydrate is said to produce an increased shelf life of the powder, and a more satisfactory dimensional stability of the gel.

A fluoride, such as potassium titanium fluoride, is added to ensure a hard, dense stone cast surface. In proper concentrations, fluoride salts are accelerators for the setting gypsum products.

One impression material, which originated in Japan, uses triethanol amine alginate, soluble and insoluble carbonate (instead of a phosphate), and calcium sulfate. So far as is known, all of the commercial formulas include calcium sulfate as the reactor.

Other alginate dental impression materials have the following formulations:

| Ingredients: | Regular Setting Material | Fast Setting Material |
|---|---|---|
| Gypsum ($CaSO_4 \cdot 2H_2O$) | 11.0 | 10.1 |
| Sodium hexafluorosilicate | 2.6 | 2.7 |
| Sodium pyrophosphate | 1.4 | 1.0 |
| Potassium alginate | 16.8 | 9.6 |
| Sodium alginate | 0 | 7.5 |
| Flavor | 0.7 | 0.7 |
| MgO | 2.4 | 2.4 |
| Diatomaceous earth | 59.5 | 60.3 |
| Zinc oxide | 3.4 | 3.5 |
| Propylene glycol | 1.1 | 1.1 |
| Glycerine | 1.1 | 1.1 |
| Total | 100 | 100 |

The manner of creating the above formulations such as the Regular Setting Material and the Fast Setting Material, involves mixing the ingredients in any order so long as the mixing is thorough. In some cases, an ingredient may tend to lump up in the mixing operation, and in those cases it may prove more desirable to premix that ingredient with another of the ingredients, and then add the premix to the rest of the ingredients in the formulation during the mixing operation. For example, zinc oxide has in some circumstance shown to clump up when it is not premixed with sodium alginate. The order of addition is not critical. Good results are achieved by combining all of the ingredients at one time in the mixer or by separately adding the ingredients during the mixing operation. Mixing of the ingredients can be effected in any heavy duty dry solids blender such as V cone blender.

Because of shelf life stability problems, alginate impression materials should be stored in cool, dry environments, preferably at a temperature below 50° C.

The fibrils in an alginate gel are assumed to be held together by primary bonds rather than by intermolecular forces, as in the case of reversible hydrocolloids. When the alginic acid is changed to a soluble salt, such as sodium alginate, the cation is attached at a carboxyl group to form a salt. When the insoluble salt is formed by the reaction of the sodium alginate in solution with a calcium salt, for example, the calcium ion exchanges with sodium ions in two adjacent molecules to produce cross-linking between the two molecules. As the reaction progresses, a cross-linked molecular complex or polymer network forms. Such a network can constitute the brush heap structure of the gel.

The best method for the user to control the gelation time is to alter the temperature of the water for mixing the alginate material. The higher the temperature of the water mixed with the alginate formulation the shorter is the gelation time. Conversely, the lower the water temperature, the longer the gelation time.

It is the object of this invention to provide a method for bonding a denture to a jaw (a term that is used herein to cover the tissue components of the oral cavity that cover the jaw such as the gums and the oral mucous membrane).

Another object of this invention is to provide an alginate irreversible hydrocolloid at the interface between the base of a denture and the contiguous jaw component.

A further object of this invention is to provide a safe liquid relining film at the interface of the denture base and the contiguous jaw component which after undergoing flow within the interface in order to achieve such relining, sets to a cushiony solid that can be easily and safely removed from the base of the denture and the jaw.

These and other objectives are met by the process of this invention.

THE INVENTION

This invention relates to a thin film denture aid derived from a relatively thin film of a liquid irreversible hydrocolloid of an alginate dental impression formulation and a process for bonding a denture to the tissue surfaces of the jaw over which the denture is superimposed during use. The process involves the steps of providing at the interface of the denture and the jaw's tissues, a liquid irreversible hydrocolloid of an alginate dental impression formulation, applying pressure to the denture so that it presses into the tissue surfaces and causes the liquid hydrocolloid to flow within such interface and thus form a cushiony film that is thicker where it is necessary to be thicker and thinner where it is necessary to be thinner, and then allowing the hydrocolloid to solidify within the interface to form the relatively thin film denture aid of the invention. When wearing of the denture is completed, i.e., after providing bonding aid for up to about 24 hours, the denture is removed, as well as any light residue of the solidified hydrocolloid from the base of the denture and on the jaw tissues. The light residue is easily and cleanly removed from the denture and the jaw tissues, without rubbing, scrubbing, and the like activities.

In a further aspect of the invention, the process comprises applying a water dispersible alkali metal alginate composition, preferably a powder composition, that is capable of forming an irreversibly settable hydrocolloid, onto the base section of an denture, allowing the composition to mix with water (or saliva) thereby causing the composition to form a liquid irreversible hydrocolloid, inserting the denture containing the wet composition thereon into the oral cavity and in contact with the jaw tissue surfaces where the denture is designed to reside, applying sufficient pressure on the denture so that the liquid irreversible hydrocolloid is distributed within the interface between the denture and the jaw tissue surfaces as a relatively thin film as characterized above, allowing the hydrocolloid film to set to a solid state and form a cushiony relining film within the interface. After the denture is removed, the solidified hydrocolloid neither adheres to the tissue surfaces nor the denture base and therefore is easily wiped off such surfaces.

The invention provides a method for bonding a denture to a jaw (a term that is used herein to cover the tissue components of the oral cavity that cover the jaw such as the gums, palate and the oral mucous membrane) using an alginate irreversible hydrocolloid at the interface between the base of a denture and the contiguous jaw component. This invention employs a safe liquid relining film at the interface of the denture base and the contiguous jaw component, which after undergoing flow within the interface in order to achieve such relining film, sets to a solid cushiony relatively-thin film that can be easily and safely removed from either the base of the denture and the jaw. The dried alginate film does not create a messy, difficult-to-remove film that is so annoying to users of the conventional denture bonding aids, as described hereinabove.

The dried alginate film of the process of the invention is not an adhesive. Its sole function is to act as a temporary cushiony reliner that significantly eliminates the void spaces between the denture base and the tissue surfaces of the jaw on which the denture is to reside. As a temporary relining film, the film is distributed within the denture-jaw interface such that a greater amount of film is located where. voids exist within the interface. As a result, the film created interface between the jaw tissues and the denture's base surface allows a relatively tight cushiony (resilient) fit between the jaw tissues and the denture's base surface. This maximizes the fit of the denture on the jaw tissue surfaces, and results in excellent adherence of the denture to the jaw tissue without the temporary relining film acting as an adhesive to either surface.

BRIEF DESCRIPTION OF THE DRAWINGS

FIG. 1 is a modified perspective view showing the deposition of particulate material that on hydration forms the aforementioned hydrocolloid, onto the base surfaces of the palate covering portion of a full denture.

FIG. 2 is a modified perspective view showing the deposition of particulate material that on hydration forms the aforementioned hydrocolloid, onto the base surfaces of the gum covering portion of a full denture.

DETAIL DESCRIPTION OF THE INVENTION

This invention involves inter alias the use of a thin, solid, alginate-denture impression material film as a denture bonding aid. The thickness of the film is variable and follows the contours of the denture's base and the tissue surface with which the denture and film are in contact. The film may range in thickness from about 0.5 to about 250 mils, and typically from about 1 to about 200 mils. The bonding aid composition of this invention contains at least three reactive solid particulate reactive components: (1) the "reactor" component, (2) a water dispersible alkali metal alginate component and (3) the "retarder" component. Preferably, the water dispersible alkali metal alginate component is a powder in which the alkali metal is one or more of lithium, sodium, potassium, ruthenium and cesium, preferably sodium and potassium. The reactor component is a solid particulate alkaline earth metal salt of a strong mineral acid that can enter into an exchange reaction with the alkali metal alginate whereby the alkaline earth metal of the alkaline earth metal salt substitutes for a sufficient amount of the alkali metal of the alginate whereby the resulting alginate is crosslinked. Preferably, the alkaline earth metal is one or more of barium, calcium, magnesium, and the like. Most preferably, the reactor is calcium sulfate (e.g., gypsum). In addition, the composition also contains a retarder, as described above. They include alkali metal (e.g., Li, Na, K, Ru and Cs) salts of weaker acids than the acid used in the reactor, such as sodium or potassium phosphate, oxalate, or carbonate. Trisodium phosphate, sodium tripolyphosphate, and tetrasodium pyrophosphate have been extensively employed for this purpose, but the latter two are now most commonly employed in denture impression materials.

The amount of the alkali metal alginate in the formulation ranges from about 5 weight percent to about 30 weight percent, basis weight of the total composition.

The amount of the reactor component in the composition ranges should be sufficient to provide sufficient crosslinking in the alginate after the exchange reaction of alkaline earth metal for alkali metal to provide the desired irreversible hydrocolloid composition at the denture-tissue interface. Typically, that amount will range from about 5 to about 25 weight percent by weight of the total composition.

The amount of retarder in the composition is variable and dependent on the amount of delay in the rate of crosslinking desired in the hydrocolloid composition during the filming operation of the process of the invention. Typically, that amount ranges from about 1 to about 5 weight percent by weight of the total composition.

Retarders may not be necessary in the formulation if the rate of the exchange reaction is slowed up by the selection of an alkaline earth metal salt in which the anion thereof is derived from an acid that is less acidic than sulfuric acid, and more acidic than phosphoric acid.

The other ingredients include enough filler in the composition to reduce or eliminate tackiness in the resulting hydrocolloid. Typically, the amount of filler ranges from about 40 to 70 weight percent basis total weight of the composition. Desirable filler materials include diatomaceous earth, zinc oxide, magnesium oxide and the like filler materials.

A fluoride, such, as potassium titanium fluoride, sodium hexafluorosilicate and the like, may be added to the composition if it is desired to ensure a hard, dense surface in the film. In proper concentrations, fluoride salts are accelerators for the setting gypsum products.

The preferred compositions in the practice of the process of the invention are described above as the "Regular Setting Material" and the "Fast Setting Material." The most preferred composition is the Regular Setting Material.

The alginate dental impression material is a powder that can be applied from a container onto the denture base substrate. The denture base substrate can be wet with water (or saliva) before application of the powder. This is illustrated in FIGS. 1 and 2. In FIG. 1, the elements 1 of the invention comprise the particulate material 5 which is deposited from a squeeze bottle 3 onto the base surfaces 7 of the palate covering portion of a full denture 2. In FIG. 2 the elements 10 of the invention comprise the particulate material 15 which is deposited from a squeeze bottle 13 onto the base surfaces 17 of the gum covering portion of a full denture 12.

In each of the illustrations above, the denture base surfaces can be wetted with water first before the application of the powdered denture impression material. Then the denture is applied to the oral cavity to its designed position over the intended jaw portion, such as over the lower or upper gums, or the palate. It is preferred that the powder have sufficient opportunity to be fully wetted by water while on the denture base surface so that at least a portion of the powder is converted into a liquid hydrocolloid. Then the denture is forced onto the designed jaw portion and the hydrocolloid is caused to redistribute on the denture base surface to effect relining of the denture base. Upon solidification, the denture is comfortably held onto the jaw for an extended period of time.

Though this invention has been described with considerable detail, it is not intended that the invention should be limited thereto.

What is claimed is:

1. A process for bonding a denture to the tissue surfaces of the jaw over which the denture is superimposed during use which consists essentially of the steps of providing at the interface of the denture and the jaw's tissues, a liquid irreversible hydrocolloid of an alginate dental impression formulation, applying pressure to the denture so that it presses into the tissue surfaces and causes the liquid hydrocolloid to flow within such interface, and then allowing the hydrocolloid to solidify within the interface.

2. The process of claim 1 wherein at the completion of the wearing of the denture, the denture is removed, as well as any light residue of the solidified hydrocolloid from the base of the denture and on the jaw tissues.

3. The process of claim 1 wherein the alginate dental impression formulation contains at least three reactive solid particulate reactive components: (1) a reactor component, (2) a water dispersible alkali metal alginate component and (3) a retarder component.

4. The process of claim 3 wherein the alginate dental impression formulation is a powder in which the alkali metal alginate is one or more of lithium, sodium, potassium, ruthenium and cesium in powder form.

5. The process of claim 4 wherein the alkali metal is one or more of sodium and potassium.

6. The process of claim 5 wherein the alkali metal is sodium.

7. The process of claim 3 wherein the reactor component is a solid particulate alkaline earth metal salt of a strong mineral acid that can enter into an exchange reaction with the alkali metal alginate whereby the alkaline earth metal of the alkaline earth metal salt substitutes for a sufficient amount of the alkali metal of the alginate whereby that the resulting alginate is crosslinked.

8. The process of claim 7 wherein the alkaline earth metal is one or more of barium, calcium, and magnesium.

9. The process of claim 8 wherein the alkaline earth metal salt of a strong mineral acid is a calcium sulfate.

10. The process of claim 3 wherein the retarder is an alkali metal salt of a weaker acid than the acid used in the reactor.

11. The process of claim 10 wherein the retarder is one or more of sodium or potassium phosphate, oxalate, or carbonate, trisodium phosphate, sodium tripolyphosphate, and tetrasodium pyrophosphate.

12. The process of claim 3 wherein the amount of the alkali metal alginate in the formulation ranges from about 5 weight percent to about 30 weight percent, basis weight of the total composition.

13. The process of claim 3 wherein the amount of the reactor component in the composition ranges is sufficient to provide sufficient crosslinking in the alginate after the exchange reaction of alkaline earth metal for alkali metal to provide the desired irreversible hydrocolloid composition at the denture-tissue interface.

14. The process of claim 13 wherein that amount ranges from about 5 to about 25 weight percent by weight of the total composition.

15. The process claim 3 wherein the amount of retarder in the composition is variable and dependent on the amount of delay in the rate of crosslinking desired in the hydrocolloid composition during the filming operation of the process.

16. The process of claim 15 wherein the amount of retarder ranges from about 1 to about 5 weight percent by weight of the total composition.

17. The process of claim 1 wherein the alginate dental impression formulation has one of the following formulations:

| Ingredients: | Regular Setting Material | Fast Setting Material |
| --- | --- | --- |
| Gypsum (CaSO$_4$.2H$_2$O) | 11.0 | 10.1 |
| Sodium hexafluorosilicate | 2.6 | 2.7 |
| Sodium pyrophosphate | 1.4 | 1.0 |
| Potassium alginate | 16.8 | 9.6 |
| Sodium alginate | 0 | 7.5 |
| Flavor | 0.7 | 0.7 |
| MgO | 2.4 | 2.4 |
| Diatomaceous earth | 59.5 | 60.3 |
| Zinc oxide | 3.4 | 3.5 |
| Propylene glycol | 1.1 | 1.1 |
| Glycerine | 1.1 | 1.1 |
| Total | 100 | 100 |

18. A process for bonding a denture to the tissue surfaces of the jaw tissues over which the denture's base is superimposed during use, which comprises applying a water dispersible alkali metal alginate composition onto the base section of the denture, allowing the composition to mix with water thereby causing the composition to form a liquid irreversible hydrocolloid, inserting the denture containing the hydrocolloid thereon into the oral cavity and in contact with the jaw tissue surfaces where the denture is designed to reside, applying sufficient pressure on the denture so that the liquid irreversible hydrocolloid is distributed within the interface between the denture and the jaw tissue surfaces, allowing the hydrocolloid to set to a solid state and form a relining film within the interface.

19. The process of claim 19 wherein the water dispersible alkali metal alginate composition is a powder that is capable of forming an irreversibly settable hydrocolloid.

20. The process of claim 19 wherein after the denture is removed, the solidified hydrocolloid neither adheres to the tissue surfaces nor the denture base and is easily wiped off such surfaces.

21. A process of bonding a denture to the jaw tissue components of the oral cavity that comprise one or more of gums, palate and the oral mucous membrane which comprises applying an alginate irreversible hydrocolloid-forming composition at the interface between the base of a denture and the contiguous jaw component and forming a safe liquid relining film at the interface which after undergoing flow within the interface achieve relining of the denture's base, and sets to a solid that can be easily and safely removed from either the base of the denture and the jaw tissue components.

22. A relatively-thin film denture reliner consisting essentially of a relatively-thin film of liquid irreversible hydrocolloid of an alginate dental impression formulation.

23. The relatively-thin film denture reliner of claim 22 wherein the formulation contains at least three reactive solid particular reactive components; (1) a reactor component, (2) a water dispersible alkali metal alginate component and (3) a retarder component.

24. The relatively-thin film denture refiner of claim 23 wherein the alginate dental impression formulation is a powder in which the alkali metal alginate is one or more of lithium, sodium, potassium, ruthenium and cesium in powder form.

25. The relatively-thin film denture reliner of claim 24 wherein the alkali metal is one or more of sodium and potassium.

26. The relatively-thin film denture reliner of claim 25 wherein the alkali metal is sodium.

27. The relatively-thin film denture reliner of claim 23 wherein the reactor component is a solid particulate alkaline earth metal salt of a strong mineral acid that can enter into an exchange reaction with the alkali metal alginate whereby the alkaline earth metal of the alkaline earth metal salt substitutes for a sufficient amount of the alkali metal of the alginate whereby that the resulting alginate is crosslinked.

28. The relatively-thin film denture reliner of claim 27 wherein the alkaline earth metal is one or more of barium, calcium, and magnesium.

29. The relatively-thin film denture reliner of claim 28 wherein the alkaline earth metal salt of a strong mineral acid is a calcium sulfate.

30. The relatively-thin film denture reliner of claim 23 wherein the retarder is an alkali metal salt of a weaker acid than the acid used in the reactor.

31. The relatively-thin film denture reliner of claim 30 wherein the retarder is one or more of sodium or potassium phosphate, oxalate, or carbonate, trisodium phosphate, sodium tripolyphosphate, and tetrasodium pyrophosphate.

32. The relatively-thin film denture reliner of claim 23 wherein the amount of the alkali metal alginate in the formulation ranges from about 5 weight percent to about 30 weight percent, basis weight of the total composition.

33. The relatively-thin film denture reliner of claim 23 wherein the amount of the reactor component in the composition ranges is sufficient to provide enough crosslinking in the alginate after the exchange reaction of alkaline earth metal for alkali metal to provide the desired irreversible hydrocolloid composition at the denture-tissue interface.

34. The relatively-thin film denture reliner of claim 33 wherein that amount ranges from about 5 to about 25 weight percent by weight of the total composition.

35. The relatively-thin film denture reliner of claim 23 wherein the amount of retarder in the composition is variable and dependent on the amount of delay in the rate of crosslinking desired in the hydrocolloid composition during the filming operation of the process.

36. The relatively-thin film denture reliner of claim 35 wherein the amount of retarder ranges from about 1 to about 5 weight percent by weight of the total composition.

37. The relatively-thin film denture reliner of claim 22 wherein the alginate dental impression formulation has one of the following formulations:

| Ingredients: | Regular Setting Material | Fast Setting Material |
| --- | --- | --- |
| Gypsum ($CaSO_4 \cdot 2H_2O$) | 11.0 | 10.1 |
| Sodium hexafluorosilicate | 2.6 | 2.7 |
| Sodium pyrophosphate | 1.4 | 1.0 |
| Potassium alginate | 16.8 | 9.6 |
| Sodium alginate | 0 | 7.5 |
| Flavor | 0.7 | 0.7 |
| MgO | 2.4 | 2.4 |
| Diatomaceous earth | 59.5 | 60.3 |
| Zinc oxide | 3.4 | 3.5 |
| Propylene glycol | 1.1 | 1.1 |
| Glycerine | 1.1 | 1.1 |
| Total | 100 | 100 |

* * * * *